(12) United States Patent
Edmondson

(10) Patent No.: US 7,074,363 B2
(45) Date of Patent: Jul. 11, 2006

(54) **SANITIZING COMPOSITION CONTAINING CHLORINATED ISOCYANURATE FOR *IN-OVO* INJECTION EQUIPMENT**

(75) Inventor: Paul Stephen Edmondson, Waterford (IE)

(73) Assignee: Infowise Limited, Wexford (IE)

( * ) Notice: Subject to any disclaimer, the term of this patent is extended or adjusted under 35 U.S.C. 154(b) by 164 days.

(21) Appl. No.: 10/436,167

(22) Filed: May 13, 2003

(65) Prior Publication Data

US 2003/0202903 A1 Oct. 30, 2003

Related U.S. Application Data

(63) Continuation of application No. PCT/IE01/00143, filed on Nov. 14, 2001.

(30) Foreign Application Priority Data

Nov. 16, 2000 (IE) ................................. 2000/0924

(51) Int. Cl.
*A61L 2/00* (2006.01)
(52) U.S. Cl. .............................. 422/37; 119/6.8; 422/1; 422/29; 510/224; 510/381
(58) Field of Classification Search ................ 422/1, 422/37, 29; 119/6.8; 510/191, 194; 424/76.5; 134/22.1
See application file for complete search history.

(56) References Cited

U.S. PATENT DOCUMENTS

| 4,265,847 | A | * | 5/1981 | Hunt et al. ................. 264/122 |
| 4,664,836 | A | * | 5/1987 | Taylor et al. ............... 510/196 |
| 5,114,647 | A | | 5/1992 | Levesque et al. ........... 264/115 |
| 5,817,320 | A | * | 10/1998 | Stone ....................... 424/278.1 |
| 5,958,334 | A | * | 9/1999 | Haddon ......................... 422/5 |
| 6,240,877 | B1 | * | 6/2001 | Bounds ....................... 119/6.8 |
| 6,397,862 | B1 | * | 6/2002 | DeSenna et al. ........... 134/22.1 |
| 6,682,754 | B1 | * | 1/2004 | Emery et al. ............... 424/426 |

FOREIGN PATENT DOCUMENTS

| EP | 0230133 A1 | 7/1987 |
| FR | 2575637 | 7/1986 |
| GB | 1505738 | 3/1978 |
| GB | 2242130 A | 9/1991 |

OTHER PUBLICATIONS

Patent Abstracts of Japan, vol. 6, No. 19, Feb. 3, 1982 & JP 56 142210 A (Shikoku Chem Corp), Nov. 6, 1981.

\* cited by examiner

*Primary Examiner*—Krisanne Jastrzab
(74) *Attorney, Agent, or Firm*—Jacobson Holman PLLC

(57) ABSTRACT

A water soluble sanitizing composition includes a chlorinated isocyanurate and an effervescent alkali base, the effervescent base including sodium carbonate agent, adipic acid and sodium bicarbonate in a weight ratio of approximately 1:1:1 to provide a sanitizing solution having a pH of from 6.8 to 7.4. A method for sanitizing a product such as in-ovo injection equipment includes the step of dissolving the composition in water to form a sanitizing solution and flushing the in-ovo injection equipment with the sanitizing solution prior to each in-ovo injection.

13 Claims, 1 Drawing Sheet

US 7,074,363 B2

SANITIZING COMPOSITION CONTAINING CHLORINATED ISOCYANURATE FOR IN-OVO INJECTION EQUIPMENT

This is a continuation of PCT/IE01/00143 filed Nov. 14, 2001 and published in English.

INTRODUCTION

The invention relates to a sanitising composition and in particular to a sanitising composition which allows for an effective and non-toxic sanitising of products such as in-ovo injection equipment.

Automated in-ovo injection systems enable the delivery of biological and pharmaceutical products directly into chick embryos, whilst still in the egg. Such injection systems can typically inoculate between 20,000 and 50,000 eggs per hour, eliminating the need to manually inject chicks after they have hatched. Such systems improve productivity in the hatcheries, and result in the production of healthier birds.

During the operation of the in-ovo injection equipment, typically one hundred eggs are injected on each process occasion. After each injection it is necessary to flush the lines, needles and the egg surfaces with a suitable sanitiser, to prevent contamination by microbiological pathogens on the surfaces of the equipment and eggs.

Existing procedures involve the use of a sanitiser such as sodium hypochlorite. However, there are a number of serious disadvantages in the use of such a product and similar products such as calcium hypochlorite. Hypochlorites are alkaline products having a pH typically greater than pH8.5. At these high pH levels the product is toxic to the chick embryo. It is therefore necessary to buffer the pH by adding an acid immediately prior to use.

Currently the standard hand-mixed sanitiser solutions may consist of a mixture of 5% sodium hypochlorite diluted in water to give an operating solution strength of 0.5%. Separately, an acid solution is made up to buffer the 0.5% sodium hypochlorite solution to lower the pH. For example citric acid may be dissolved in water and 5% sodium hypochlorite added to the acid solution to give a final solution of 0.5% sodium hypochlorite.

Such hand-mixed sanitising solutions are however unsatisfactory for reliably disinfecting the in-ovo equipment for a number of reasons.

Commercial hypochlorite products are available from 1% to over 10% available chlorine. There are no standard solutions available. Because many of these products are used for non-critical purposes (for example, for household uses), the strengths of the products are inconsistent. It is also well known that hypochlorite products are unstable, losing their potency in storage. Where the solution strength is not known with absolute confidence it is necessary to chemically analyse the hypochlorite products to determine the precise strength of the product before making up sanitiser solutions which are used for critical purposes such as sanitising in ovo equipment.

In addition, when buffered to the desirable pH with a suitable acid, the resultant sanitiser solution is highly unstable, losing about 30% of its strength in one day and up to 70% of its strength in two days.

The procedure for making up the in-ovo sanitising solutions using commercial hypochlorite products is also complex, time-consuming and is prone to costly mistakes and errors, leading to potential pathogenic contamination of the eggs and embryos.

There is therefore a need for an improved stable sanitiser composition which is effective, in particular for sanitising equipment, especially in ovo injection equipment in a non-toxic and efficient manner.

STATEMENTS OF INVENTION

According to the invention there is provided a water soluble sanitising composition comprising a chlorinated isocyanurate and an effervescent base, the effervescent base comprising an alkali buffering agent, an aliphatic carboxylic acid and an alkali metal bicarbonate to provide a sanitising solution having a pH of from 6.8 and 7.4.

The invention also provides a water soluble sanitising composition comprising a chlorinated isocyanurate and an alkali effervescent base, the effervescent base comprising an alkali buffering agent, an aliphatic carboxylic acid and an alkali metal bicarbonate to provide a sanitising solution having a pH of from 6.8 to 7.4.

According to another aspect the invention provides a water soluble sanitising composition comprising a chlorinated isocyanurate, an aliphatic carboxylic acid, an alkali buffering agent and an alkali metal bicarbonate to provide a sanitising solution having a pH of from 6.8 to 7.4.

The invention also provides a water soluble sanitising composition comprising a chlorinated isocyanurate, adipic acid, an alkali buffering agent and an alkali metal bicarbonate. The composition preferably provides a sanitising solution having a pH of from 6.8 to 7.4.

In a further aspect die invention provides a water soluble sanitising composition comprising a chlorinated isocyanurate, and an effervescent alkali base, the effervescent base comprising adipic acid, an alkali buffering agent and an alkali metal bicarbonate. The composition preferably provides a sanitising solution having a pH of from 6.8 to 7.4, ideally approximately 7.0.

In a particularly preferred embodiment the alkali metal bicarbonate is sodium bicarbonate. The particular advantages of utilising sodium bicarbonate are that it is very soluble in water, it is suitable for use in effervescent preparations, it is available in pharmaceutical or food grade and produces alkaline solutions.

Preferably the alkali effervescent base comprises sodium carbonate as an alkali buffering agent, adipic acid as an aliphatic carboxylic acid and sodium bicarbonate in an approximate weight ratio of 1:1:1, most preferably approximately 20:19:19. These ratios surprisingly produce good quality effervescent tablets with controlled release of solutions of a narrow band of pH values over a time period, and with stable release of available chlorine over a time period.

Preferably die chlorinated isocyanurate is sodium dichloroisocyanurate. Sodium dichloroisocyanurate is readily soluble in water, producing solutions that are effective sanitisers and, more particularly in relation to this invention, remain active over a wide range of pH.

In a preferred embodiment the alkali buffering agent is sodium carbonate. In a particularly preferred aspect die sodium carbonate buffering agent is an admixture of sodium carbonate in a granular form and sodium carbonate in a powder form. Sodium carbonate is readily soluble in water, is available in pharmaceutical or food grades and is strongly alkaline.

In this case preferably the weight ratio of granular sodium carbonate to powder sodium carbonate is between 60:40 and 90:10. The choice of tie particular admixture of granular and powder materials enables the production of a stable effervescent tablet of acceptable disintegration characteristics, whilst retaining the opportunity for processing by direct compression.

In a preferred embodiment the aliphatic carboxylic acid is adipic acid. Adipic acid has the advantage of being non hygroscopic, which helps to preserve the integrity and stability of the finished formulation, and also the material has lubricating properties that aid the tabletting process.

The composition of the invention preferably delivers approximately 0.5% available chlorine. A 0.5% available chlorine solution has the wide-spectrum activity necessary for effective sanitation, being effective against spores, viruses, mycobacteria, bacteria and fungi.

In a particularly preferred embodiment the composition is in the form of a water soluble tablet. The effervescent tablet format has the advantages of being in a unit dose format, which self-dissolves in water, to produce sanitiser solutions of known and accurate strength, without having to weigh out powders, measure out liquids and to compute die required dosage and solution strength. Tablets are easier and safer to handle and store, and they do not spill.

According to another aspect the invention provides a water soluble sanitising composition comprising a chlorinated isocyanurate and an effervescent base, the effervescent base comprising sodium carbonate, adipic acid and sodium bicarbonate in an approximate weight ratio of 1:1:1.

The composition is preferably formed by a direct compression technique, which enables the manufacture of tie alkali effervescent tablets without pre-processing by granulation and drying of the ingredients or addition of tabletting aids.

The invention also provides a method for sanitising comprising the single step of dissolving a composition of the invention in water and flushing, immersing or dipping product to be sanitised in the sanitising solution. Preferably the composition is in a water soluble tablet form. The product may be eggs or in ovo injection equipment.

The invention further provides a method for sanitising in-ovo injection equipment comprising the single step of dissolving a composition of the invention in water to form a sanitising solution. The sanitising solution is then flushed through the lines and needles and over the egg surfaces prior to each in-ovo injection. Preferably the sanitising solution comprises a chlorinated isocyanurate.

The invention also provides a method for sanitising eggs comprising dissolving a composition of the invention in water to form a sanitising solution and flushing, immersing or dipping the eggs in the sanitising solution.

The invention further provides a process for preparing a water soluble sanitising composition comprising the step of directly compressing into water soluble effervescent tablets a chlorinated isocyanurate such as sodium dichloroisocyanurate, an alkali buffering agent such as sodium carbonate, an aliphatic carboxylic acid such as adipic acid or salt thereof and an alkali metal bicarbonate preferably sodium bicarbonate.

Unlike many preparations known in the art, the selection of the ingredients surprisingly forms a tablet with desirable physical characteristics without recourse to pre-preparation of the ingredients by agglomeration and combination with wetting agents (such as water or isopropyl alcohol), which subsequently requires drying (such as with a fluid bed dryer), and/or compacting and/or granulating, and without the addition of tabletting aids (such as sorbitol, salts of stearates, salts of lauryl sulphate, Emcosoy, polyetheylene glycol, sodium benzoate and similar).

BRIEF DESCRIPTION OF THE DRAWINGS

The invention will be more clearly understood from the following description of some embodiments thereof, given by way of example only with reference to the accompanying drawings in which.

DETAILED DESCRIPTION

Figure 1:
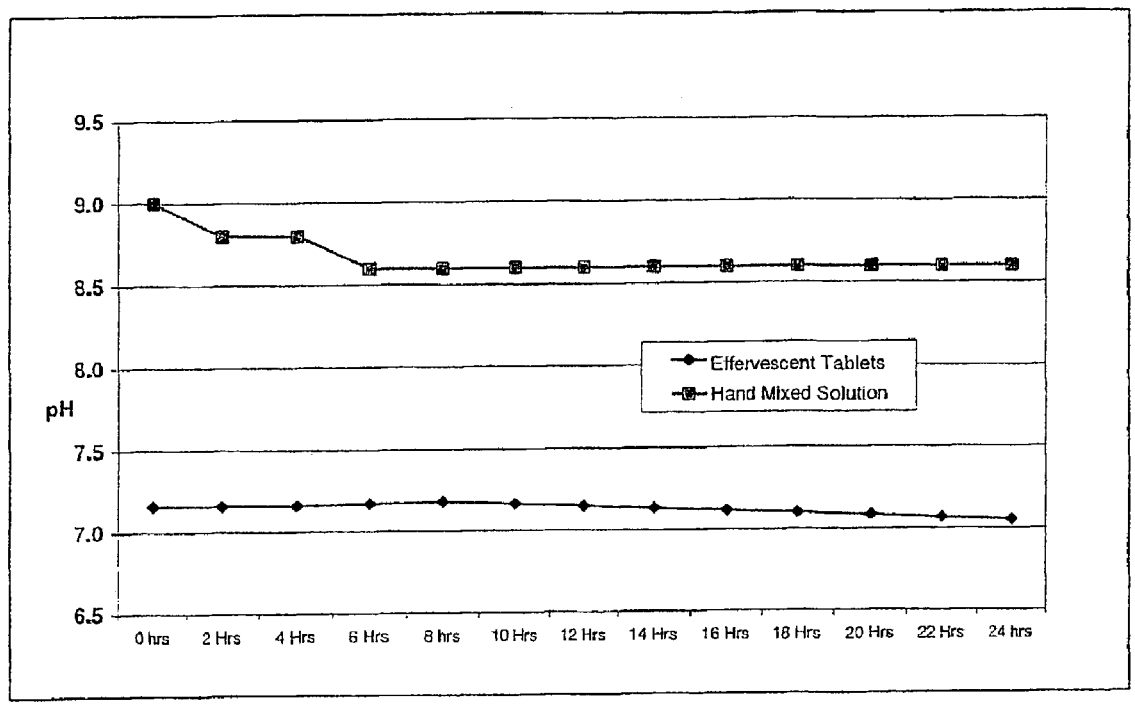
FIG. 1 is a graph showing the change in pH over time (hours) for a hand mixed solution in comparison to effervescent tablets of the invention.

Chlorinated isocyanurates are well known chlorine donors used as swimming pool disinfectants and in formulations used for dishwashing, laundry products or disinfection of baby feeding bottles.

Of the chlorinated isocyanurates available, the most suitable are those with the greatest solubility, such as sodium or potassium dichloroisocyanurate.

The present invention provides a water soluble composition comprising a chlorinated isocyanurate and an alkali buffering effervescent base, which provides a non-toxic solution having a pH from between 6.8 and 7.4. This is a pH range that is compatible with the embryotic fluid or air sac of a poultry egg. The composition may be used in sanitising equipment, in particular for sanitising in ovo injection equipment. The composition is very stable in solution and simple to use.

The composition of the invention may be produced in a solid dose form. A solid dose form eliminates the necessity to weigh out a quantity of powder or granules each time a sanitiser solution is required. Using a single solid dose form also ensures that a sanitising solution having an accurate and known disinfectant concentration is produced in a one step process. The handling of a solid dose form is also easier and safer than handling chlorinated powders or granules or hypochlorite solutions.

The composition may be in the form of tablets especially effervescent tablets. Effervescent tablets are preferred because they disperse quickly in solution and dissolve the active ingredient. There is no need to crush the tablets and/or stir the solutions to achieve a clear sanitising solution within a reasonable time period.

The effervescent tablets comprise an active ingredient such as a chlorinated isocyanurate and an inert, effervescent base. The inert, effervescent base typically comprises an aliphatic carboxylic acid or salt thereof such as fumaric acid or adipic acid and an alkali metal carbonate or bicarbonate such as sodium bicarbonate.

However, effervescent tablets from such a typical formulation producing a sanitiser solution of approximately 0.5% available chlorine strength, produce solutions with a pH of approximately 5.5 to 6.5, and typically approximately pH6.0. Such pH values are too acidic and are toxic to chick embryos.

To achieve a pH which is compatible and non-toxic to the embryotic fluid or air sac of a chick egg the effervescent tablets include a buffering agent to increase the pH to approximately pH 7.0. The formulation to include a buffering agent in accordance with this invention does not inhibit the tabletting quality and the composition remains easy to compress into tablet form by a direct compression process.

The tablet disintegrates in solution within reasonable time producing a clear working solution. Most importantly the addition of the buffering agent does not inhibit the disinfection capability of the sanitising solution.

Buffering agents of choice must be non-toxic, readily soluble, non-oxidisable and commercially available. Examples suitable for use in the present invention include sodium or potassium hydroxide, sodium tripolyphosphate, trisodium phosphate, sodium carbonate, and the ortho- and metasilicates.

It was found that the use of powdered sodium carbonate in total produces a tablet of poor physical quality. Similarly, a formulation using granular sodium carbonate also produced a tablet of poor physical qualities. The term granular in the specification is taken to encompass compounds having a granular grade giving a typical sieve analysis of:

| Micron | % Retained |
|--------|------------|
| 2800   | 1.5%       |
| 425    | 28.3%      |
| 250    | 44.9%      |
| 125    | 22.0%      |
| 63     | 2.0%       |
|        | QS         |

It was surprisingly found that an admixture containing both granular and powder sodium carbonate produced a tablet of good physical characteristics by a direct compression process and without the addition of the usual tabletting aids. An admixture where the ratio of granular sodium carbonate to powder sodium carbonate is between 60:40 and 90:10 produced a tablet of excellent physical characteristics.

Tablets prepared using such an admixture of sodium carbonate have been shown to have good disintegration properties, produce clear sanitising solutions and are stable at normal atmospheric conditions.

A critical factor of stabilisation is the pH of the sanitising solution so prepared. Without stable control of the pH in parallel with the desired target pH of the embryotic fluid or air sac, toxic reactions may result in poor hatchability of the chicks from the eggs. The following results demonstrate the remarkable pH control of the current invention, compared especially to the current hand-mixed method when using sodium hypochlorite liquid, buffered with citric acid.

The pH of the Hand Mixed solution started at pH9 reducing to pH8.6 after 6 hours, where it stabilised over the balance of the 24 hour period (FIG. 1). The effervescent tablet of the current invention commenced with a pH of 7.16 rising to 7.18 after 8 hours and reducing to 7.05 after 24 hours. The tablet had a stabilised pH in the range of 7 to 7.2, which is ideally compatible with the egg air sac—thus protecting against potential toxicity problems and, therefore, assisting the maximisation of hatchability.

The choice of the sodium carbonate also significantly contributes to the effervescent nature of the formulation.

It is also envisaged that the composition of the invention may be prepared in other solid dose forms, for example in particulate form sealed within a sachet which dissolves in a known volume of water to provide a known concentration of sanitising solution.

The invention will be more clearly understood from the following description given by way of example.

EXAMPLE 1

Tablets are prepared having the following formulation by weight. The formulation given is for a single tablet.

| Sodium dichloroisocyanurate | 42% |
| Sodium bicarbonate          | 19% |
| Adipic acid                 | 19% |
| Sodium carbonate            | 20% |

8.15 g sodium dichloroisocyanurate, 3.75 g sodium bicarbonate, 3.59 g adipic acid and 3.76 g of sodium carbonate are weighed out and dry blended together. The dry blend is then compressed by direct compression (on chrome plated tooling) into tablets.

EXAMPLE 2

The hatchability of live embryos transferred was measured in approximately 50-egg replicates per trial per treatment. Two identical trials were conducted. Eggs were either not injected or were air cell injected with either 30 or 300 μl volume, using a hand-mixed sanitiser composition (comprising per liter of water: 106 mg sodium bromide, 1.19 grams citric acid and 106 ml of 5.5% hypochlorite), an effervescent tablet of Example 1 and saline. The chicks (n=108) were grown out in brooder batteries for one week and monitored for mortality. With the exception of the non-injected controls, the treatment combinations were appropriate for a two-way factorial analysis in which material and volume were both evaluated. The two-way factorial analysis was then conducted using the previous trial as a blocking factor. Table 1(a) and (b) illustrate the results of hatchability and late embryotic mortality results in the two identical trials. Table 2 contains the results pooled across both trials. Results are shown for live and late dead hatch, live pip and dead pip. (Pip refers to a bird that has not completely emerged from the shell).

The hatchability results are based on necropsy of hatch residue.

The results show no significant interactions.

TABLE 1(a)

| Trial 1 | | | Hatch of live | Late Dead | Live Pip | Dead Pip |
|---------|---|---|------|-----------|----------|----------|
| Not Inj. | None | Mean | 96.94 | 0.52 | 0.51 | 0.51 |
|          |      | SD   | 3.53  | 1.04 | 1.02 | 1.02 |
|          |      | n    | 4     | 4    | 4    | 4    |
| Std. Hand Mix | 30 μl | Mean | 97.37 | 0.00 | 1.58 | 0.00 |
|          |      | SD   | 3.14  | 0.00 | 2.03 | 0.00 |
|          |      | n    | 4     | 4    | 4    | 4    |
|          | 300 μl | Mean | 96.84 | 1.02 | 1.06 | 0.00 |
|          |      | SD   | 1.22  | 2.04 | 1.22 | 0.00 |
|          |      | n    | 4     | 4    | 4    | 4    |
| Effervescent Tablets | 30 μl | Mean | 95.23 | 0.00 | 2.11 | 0.00 |
|          |      | SD   | 2.68  | 0.00 | 1.70 | 0.00 |
|          |      | n    | 4     | 4    | 4    | 4    |
|          | 300 μl | Mean | 98.90 | 0.00 | 0.56 | 0.54 |
|          |      | SD   | 1.27  | 0.00 | 1.11 | 1.09 |
|          |      | n    | 4     | 4    | 4    | 4    |
| Saline   | 30 μl | Mean | 94.80 | 2.04 | 1.01 | 1.53 |
|          |      | SD   | 3.54  | 1.67 | 1.17 | 1.02 |
|          |      | n    | 4     | 4    | 4    | 4    |
|          | 300 μl | Mean | 96.80 | 1.12 | 1.56 | 0.52 |
|          |      | SD   | 3.58  | 1.29 | 1.99 | 1.04 |
|          |      | n    | 4     | 4    | 4    | 4    |

TABLE 1(b)

| Trial 2 | | | Hatch of live | Late Dead | Live Pip | Dead Pip |
|---|---|---|---|---|---|---|
| Not Inj. | None | Mean | 97.99 | 1.00 | 0.50 | 0.51 |
| | | SD | 1.63 | 1.15 | 1.00 | 1.02 |
| | | n | 4 | 4 | 4 | 4 |
| Std. Hand Mix | 30 μl | Mean | 97.44 | 0.52 | 0.50 | 0.00 |
| | | SD | 3.10 | 1.04 | 1.00 | 0.00 |
| | | n | 4 | 4 | 4 | 4 |
| | 300 μl | Mean | 98.00 | 0.00 | 1.00 | 0.00 |
| | | SD | 4.00 | 0.00 | 2.00 | 0.00 |
| | | n | 4 | 4 | 4 | 4 |
| Effervescent Tablets | 30 μl | Mean | 97.41 | 2.08 | 0.00 | 0.51 |
| | | SD | 0.99 | 0.04 | 0.00 | 1.02 |
| | | n | 4 | 4 | 4 | 4 |
| | 300 μl | Mean | 98.98 | 1.02 | 0.00 | 0.00 |
| | | SD | 2.04 | 2.04 | 0.00 | 0.00 |
| | | U | 4 | 4 | 4 | 4 |
| Saline | 30 μl | Mean | 98.50 | 0.00 | 0.00 | 1.00 |
| | | SD | 1.00 | 0.00 | 0.00 | 1.15 |
| | | n | 4 | 4 | 4 | 4 |
| | 300 μl | Mean | 98.49 | 0.00 | 0.50 | 1.01 |
| | | SD | 1.01 | 0.00 | 1.00 | 1.17 |
| | | n | 4 | 4 | 4 | 4 |

TABLE 2

| | | | Hatch of live | Late Dead | Live Pip | Dead Pip |
|---|---|---|---|---|---|---|
| Not Inj. | None | Mean | 97.46 | 0.76 | 0.51 | 0.51 |
| | | SD | 2.61 | 1.05 | 0.94 | 0.94 |
| | | n | 8 | 8 | 8 | 8 |
| Std. Hand Mix | 30 μl | Mean | 97.41 | 0.26 | 1.04 | 0.00 |
| | | SD | 2.89 | 0.74 | 1.59 | 0.00 |
| | | n | 8 | 8 | 8 | 8 |
| | 300 μl | Mean | 97.42 | 0.51 | 1.03 | 0.00 |
| | | SD | 2.81 | 1.44 | 1.53 | 0.00 |
| | | n | 8 | 8 | 8 | 8 |
| Effervescent Tablets | 30 μl | Mean | 96.32 | 1.04 | 1.05 | 0.26 |
| | | SD | 2.20 | 1.11 | 1.58 | 0.72 |
| | | n | 8 | 8 | 8 | 8 |
| | 300 μl | Mean | 98.94 | 0.51 | 0.28 | 0.27 |
| | | SD | 1.57 | 1.44 | 0.79 | 0.77 |
| | | n | 8 | 8 | 8 | 8 |
| Saline | 30 μl | Mean | 96.70 | 1.02 | 0.51 | 1.27 |
| | | SD | 3.08 | 1.54 | 0.94 | 1.05 |
| | | n | 8 | 8 | 8 | 8 |
| | 300 μl | Mean | 97.65 | 0.56 | 1.03 | 0.77 |
| | | SD | 2.60 | 1.04 | 1.57 | 1.06 |
| | | n | 8 | 8 | 8 | 8 |

Table 3 illustrates the results of early mortality by trial and Table 4 gives the pooled results. There were no significant interactions or main material effects.

TABLE 3

| | | % Mortality |
|---|---|---|
| | | Trial 1 |
| Not injected | None | 3.70 |
| Std Hand Mix | 30 μl | 0.93 |
| | 300 μl | 0.93 |
| Effervescent Tablets | 30 μl | 0.93 |
| | 300 μl | 0.00 |
| Saline | 30 μl | 2.78 |
| | 300 μl | 0.00 |

TABLE 3-continued

| | | % Mortality |
|---|---|---|
| | | Trial 2 |
| Not injected | None | 0.93 |
| Standard Hand Mix | 30 μl | 1.85 |
| | 300 μl | 0.00 |
| Effervescent Tablets | 30 μl | 2.78 |
| | 300 μl | 0.00 |
| Saline | 30 μl | 4.63 |
| | 300 μl | 0.00 |

TABLE 4

| | | % Mortality |
|---|---|---|
| Not injected | None | 2.31 |
| Std Hand Mix | 30 μl | 1.39 |
| | 300 μl | 0.46 |
| Effervescent Tablets | 30 μl | 1.85 |
| | 300 μl | 0.00 |
| Saline | 30 μl | 3.70 |
| | 300 μl | 0.00 |

The stability of the sanitising solutions is also a critical factor in maintaining efficacy over tie cycle of use of the egg injection equipment. The stability of the formulated tablets showed excellent characteristics, especially when compared to the standard hand-mixed product, hereinbefore described.

Figure 2:
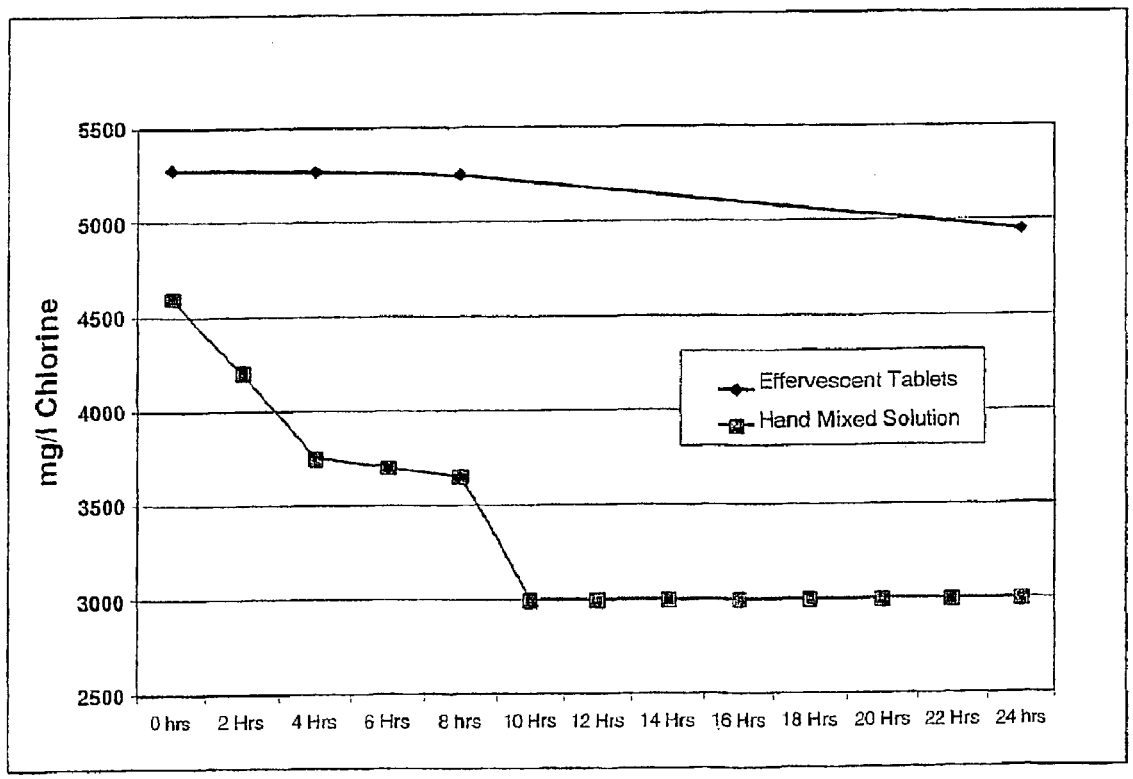
FIG. 2 is a graph showing the stability (mg/l chlorine) of a hand mixed solution in comparison to effervescent tablets of the invention.

FIGS. 3 and 4 show the stability of solutions over time. The standard Hand Mixed solution (FIG. 2) gave an initial concentration of 4,600 mg/l chlorine, which reduced to 3000 mg/l in less than 10 hours—a 35% drop. The solution had lost almost 20% of its strength after just 4 hours. Such losses could give rise to concerns with the efficacy of the product during the egg injection cycle. The effervescent tablet of the current invention gave a solution initial strength of almost 5,300 mg/l chlorine retaining a level of over 4,900 mg/l after 24 hours, with no significant change in strength over the initial 8 hours, giving an exceptional performance.

A study was also carried out to determine the stability of an approximate 0.5% available chlorine solution using the effervescent tablet of Example 1 over a 9 week period. As table 5 illustrates the solution maintained a stable pH over the 9 weeks.

TABLE 5

| Time (Weeks) | Available Chlorine (ppm) | pH | Temperature (° C.) |
|---|---|---|---|
| 0 | 4843.9 | 6.89 | 15 |
| 1 | 4434.56 | 6.96 | 14 |
| 2 | 3572.32 | 6.97 | 16 |
| 3 | 3615.87 | 6.97 | 16 |
| 4 | 3342.97 | 6.94 | 17 |
| 5 | 3070.08 | 6.93 | 18 |
| 6 | 2933.63 | 6.89 | 16 |
| 7 | 2387.84 | 7.05 | 18 |
| 8 | 2319.62 | 6.98 | 17 |
| 9 | 2046.72 | 6.95 | 18 |

The invention is not limited to the embodiments hereinbefore described which may be varied in detail.

The invention claimed is:

1. A water soluble sanitising tablet comprising a chlorinated isocyanurate and an effervescent base, wherein the tablet does not contain tabletting aids and wherein the effervescent base comprises sodium carbonate, adipic acid, and sodium bicarbonate in an approximate weight ratio of 1:1:1 to provide a sanitising solution having a pH of from 6.8 to 7.4.

2. The tablet as claimed in claim 1 wherein the weight ratio is approximately 20:19:19.

3. The tablet as claimed in claim 1 wherein the sanitising solution has a pH of approximately 7.0.

4. The tablet as claimed in claim 1 wherein the sodium carbonate is an admixture of sodium carbonate in a granular form and sodium carbonate in a powder form.

5. The tablet as claimed in claim 4 wherein the weight ratio of granular sodium carbonate to powder sodium carbonate is between 60:40 and 90:10.

6. The tablet as claimed in claim 1 wherein the composition delivers approximately 0.5% available chlorine.

7. The tablet as claimed in claim 1 wherein the tablet formed by a direct compression technique.

8. A method for sanitising comprising the steps of:

providing a water soluble sanitising tablet comprising a chlorinated isocyanurate and an effervescent base, wherein the tablet does not contain tabletting aids and wherein the effervescent base comprises sodium carbonate, adipic acid and sodium bicarbonate, in an approximate weight ratio of 1:1:1 dissolving the tablet in water to form a sanitising solution having a pH of from 6.8 to 7.4; and flushing, immersing or dipping a product to be sanitised in the sanitising solution.

9. The method as claimed in claim 8 wherein the product is in ovo injection equipment.

10. The method as claimed in claim 8 wherein the product is an egg.

11. A method for sanitising in-ovo injection equipment comprising the steps of:

providing a water soluble sanitizing tablet comprising a chlorinated isocyanurate and an effervescent base, wherein the tablet does not contain tabletting aids and wherein the effervescent base comprises sodium carbonate, adipic acid, and sodium bicarbonate in an approximate weight ratio of 1:1:1 to provide a sanitizing solution having a pH of from 6.8 to 7.4;

providing water, dissolving the tablet in water to form a sanitising solution having a pH of from 6.8 to 7.4; and flushing, immersing or dipping in-ovo injection equipment to be sanitised in the sanitising solution.

12. A method for sanitising eggs comprising the steps of:

providing a water soluble sanitising tablet comprising a chlorinated isocyanurate and an effervescent base, wherein the tablet does not contain tabletting aids and wherein the effervescent base comprises sodium carbonate, adipic acid and sodium bicarbonate in an approximate weight ratio of 1:1:1 to provide a sanitising solution having a pH of from 6.8 to 7.4;

dissolving the tablet in water to form a sanitising solution having a pH of from 6.8 to 7.4; and flushing, immersing or dipping eggs to be sanitised in the sanitising solution.

13. A process for preparing a water soluble sanitising composition comprising the step of directly compressing into water soluble effervescent tablets a chlorinated isocyanurate and an effervescent base, the effervescent base comprising sodium carbonate, adipic acid and sodium bicarbonate in an approximate weight ratio of 1:1:1 and the tablet does not contain tabletting aids.

* * * * *